United States Patent
Shibahara (10) Patent No.: US 8,110,817 B2
(45) Date of Patent: Feb. 7, 2012

(54) PROBE ARRAY AND METHOD OF MANUFACTURING THE SAME

(75) Inventor: Teruhisa Shibahara, Machida (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 408 days.

(21) Appl. No.: 12/494,736

(22) Filed: Jun. 30, 2009

(65) Prior Publication Data

US 2010/0001207 A1    Jan. 7, 2010

(30) Foreign Application Priority Data

Jul. 7, 2008   (JP) .................. 2008-176717

(51) Int. Cl.
*G01J 1/58* (2006.01)
(52) U.S. Cl. .................. 250/458.1; 250/459.1
(58) Field of Classification Search ............... 250/458.1, 250/459.1
See application file for complete search history.

(56) References Cited

U.S. PATENT DOCUMENTS

2004/0159798 A1* 8/2004 Martin et al. ............... 250/458.1

FOREIGN PATENT DOCUMENTS

| JP | 2005-081767 A | 3/2005 |
|----|---------------|--------|
| JP | 2005-249480   | 9/2005 |
| JP | 2005-345481   | 12/2005 |
| JP | 2006-126112 A | 5/2006 |
| JP | 2006-349559 A | 12/2006 |
| JP | 2007-089530 A | 4/2007 |

OTHER PUBLICATIONS

Sekine, Mitsuo,Science and Application of New DNA Chips; Jul. 30, 2007, pp. 8-9 (with English translation).

* cited by examiner

*Primary Examiner* — Mark R Gaworecki
(74) *Attorney, Agent, or Firm* — Dickstein Shapiro LLP (57) ABSTRACT

A probe array includes a probe-carrying substrate and a base member. The probe-carrying substrate has first and second principal surfaces extending parallel to each other, and a plurality of probe carriers carrying probe molecules. The base member has a reference surface extending parallel to a fluorescence-receiving surface, and a seating surface supporting the probe-carrying substrate and extending in a direction other than a direction parallel to the reference surface. The probe carriers each have a plurality of surfaces forming different angles with respect to the fluorescence-receiving surface, the plurality of surfaces including a bottom surface and uprising surfaces extending from the bottom surface. Accordingly, the plurality of surfaces have different sensitivities, realizing a wide dynamic range.

16 Claims, 11 Drawing Sheets

PROBE ARRAY AND METHOD OF MANUFACTURING THE SAME

BACKGROUND OF THE INVENTION

1. Field of the Invention

The present invention relates to probe arrays used in the fields of chemistry and biochemistry, and methods of manufacturing the probe arrays, and in particular to improvement in the certainty of detection in fluorescence observation.

2. Description of the Related Art

Deoxyribonucleic-acid (DNA) chips have been attracting attention as tools for genetic diagnosis where a plurality of items are examined simultaneously, for example, where the amounts of expressions of different messenger ribonucleic acids (mRNAs) are examined simultaneously, and where different single-nucleotide polymorphisms (SNPs) are examined simultaneously. DNA chips, also called DNA microarrays, are each a probe array in which different kinds of probes, which are known DNA molecules that hybridize with target DNA molecules and RNA molecules, are carried by a plurality of periodically arranged probe carriers.

Antigen chips and antibody chips have also been attracting attention as tools for simultaneously examining the presences of different kinds of antigens and antibodies. Antigen chips are each a probe array in which different kinds of probes, which are known antigen molecules that bond to target antibody molecules, are carried by a plurality of periodically arranged probe carriers. Antibody chips are each a probe array in which different kinds of probes, which are known antibody molecules that bond to target antigen molecules, are carried by a plurality of periodically arranged probe carriers.

One of typical methods of detecting target molecules by using such probe arrays is fluorescence observation (refer to the following for example: Sekine, Mitsuo. Atarashii DNA Chippu no Kagaku to Oyo (Science and Application of New DNA Chips); edited by Kodansha Scientific; published by Kodansha: Jul. 30, 2007; pp. 008-009). In fluorescence observation, a sample solution is first chemically processed so that target molecules are fluorescently modified. The fluorescently modified sample solution is applied to probe carriers of a probe array. Subsequently, while excitation light is applied to the sample solution, fluorescence emitted from the sample solution is observed so as to detect to which probes on the probe array the target molecules have bonded.

The probe array used in fluorescence observation is desired to be quantitative in terms of density of target molecules, regardless of whether the density of target molecules contained in the sample solution is high or low. That is, the probe array is desired to have a wide dynamic range for density of target molecules.

In the known art, however, when the density of target molecules applied to a probe array having a low sensitivity is too low, the presence of the target molecules cannot be detected because the fluorescence emitted from the probe array is too weak. Whereas, when the density of target molecules applied to a probe array having a high sensitivity is too high, the intensity of fluorescence emitted from the probe array becomes saturated, resulting in lack of quantitativeness. In this respect, there is a demand for a probe array having a wide dynamic range and being quantitative regardless of whether the density of target molecules is low or high.

To realize a wide dynamic range with a known probe array, fluorescence observation is in general performed for a plurality of times with various intensities of excitation light. In such a method, however, the need of performing a plurality of observations makes the detection operation complicated.

Moreover, after repeated applications of excitation light, fluorescence with which target molecules are modified may diminish, resulting in poor or unstable sensitivity.

To avoid such a problem, there is a demand for a probe array with which a detection result based on a wide dynamic range can be obtained in a single fluorescence observation.

SUMMARY OF THE INVENTION

Accordingly, it is an object of the present invention to provide a probe array satisfying the aforementioned demands by realizing a wide dynamic range, and a method of manufacturing the probe array.

The present invention is directed to a probe array used in detecting probe molecules by fluorescence observation, and includes the following features so as to solve the above-described technical problems.

According to a first preferred embodiment of the present invention, a probe array includes a probe-carrying substrate having first and second principal surfaces facing and extending parallel to each other, and a plurality of probe carriers arranged on the first principal surface and carrying the probe molecules; and a base member having a reference surface extending parallel to a light-receiving surface that receives, in fluorescence observation, fluorescence emitted from the probe carriers, and a seating surface being in contact with the second principal surface of the probe-carrying substrate so as to support the probe-carrying substrate.

The probe carriers each have a bottom surface parallel to the principal surfaces, and uprising surfaces extending from the bottom surface. The seating surface extends in a direction other than a direction parallel to the reference surface.

According to a second preferred embodiment of the present invention, a probe array includes a probe-carrying substrate having a reference surface and a plurality of probe carriers arranged on the reference surface, the probe carriers carrying the probe molecules.

The probe-carrying substrate is disposed such that the reference surface extends parallel to a light-receiving surface that receives, in fluorescence observation, fluorescence emitted from the probe carriers. The probe carriers each have a bottom surface and uprising surfaces extending from the bottom surface, the uprising surfaces extending in directions other than a direction perpendicular to the reference surface.

In the first and second preferred embodiments of the present invention, a surface parallel to the light-receiving surface that receives, in fluorescence observation, fluorescence emitted from the probe carriers is defined as the reference surface. In the first preferred embodiment, the base member has the reference surface. Whereas, in the second preferred embodiment, the probe-carrying substrate has the reference surface.

In the probe arrays according to the first and second preferred embodiments of the present invention, each probe carrier has a plurality of surfaces forming different angles with respect to the light-receiving surface provided for fluorescence observation. Therefore, these individual surfaces can have different sensitivities. When the density of target molecules is low, fluorescence emitted from one of the surfaces that has a relatively high sensitivity is subjected to detection. When the density of target molecules is so high that that the fluorescence intensity of the foregoing surface having the relatively high sensitivity become saturated, fluorescence emitted from another surface having a lower sensitivity than the foregoing surface is subjected to detection. Thus, quantitative fluorescence detection can be performed. Accordingly, a probe array having a wide dynamic range is realized.

In the probe array according to the first and second preferred embodiments of the present invention, the bottom surface and the uprising surfaces may include at least a first surface forming an angle θ1 with respect to the reference surface and a second surface forming an angle θ2 with respect to the reference surface and larger than the angle θ1, the angles θ1 and θ2 being determined for sides forming an angle smaller than 90 degrees therebetween. In this case, a value represented by cos θ1/cos θ2 is preferably 5 at the minimum and 50 at the maximum, or more preferably 5 at the minimum and 20 at the maximum.

By configuring the probe array according to the first and second preferred embodiments of the present invention such that the bottom surface and the uprising surfaces include at least the first surface forming the angle θ1 with respect to the reference surface and the second surface forming the angle θ2 with respect to the reference surface and larger than the angle θ1, and the value represented by cos θ1/cos θ2 is 5 at the minimum and 50 at the maximum, a dynamic range substantially the same as for currently commercially available fluorescence detectors is provided. Moreover, a significant difference is assuredly provided between the sensitivities of the first and second surfaces, and quantitativeness in the dynamic range is assuredly maintained. More specifically, if the value represented by cos θ1/cos θ2 is 20 at the maximum, quantitativeness is maintained more assuredly.

In the probe array according to the first and second preferred embodiments of the present invention, the bottom surface and the uprising surfaces may include at least first, second, . . . , and n-th surfaces forming respective angles θ1, θ2, . . . , and θn, with respect to the reference surface, the angles θ1, θ2, . . . , and θn being determined for sides forming an angle smaller than 90 degrees therebetween and being in ascending order. Further, when k denotes a natural number of 2 to n, a value represented by cos θ(k−1)/cos θk for angles θ(k−1) and θk formed with respect to the reference surface by (k−1)-th and k-th surfaces is preferably 50 at the maximum, and a value represented by cos θ1/cos θn is preferably 5 at the minimum. More preferably, the value represented by cos θ(k−1)/cos θk is 20 at the maximum, and the value represented by cos θ1/cos θn is 50 at the minimum.

By configuring the probe array according to the first and second preferred embodiments of the present invention such that the bottom surface and the uprising surfaces include at least the first, second, . . . , and n-th surfaces forming the respective angles θ1, θ2, . . . , and θn in ascending order with respect to the reference surface, and that, when k denotes a natural number of 2 to n, the value represented by cos θ(k−1)/cos θk for the angles θ(k−1) and θk formed with respect to the reference surface by the (k−1)-th and k-th surfaces is 50 at the maximum, and the value represented by cos θ1/cos θn is 5 at the minimum, a dynamic range substantially the same as for currently commercially available fluorescence detectors is provided. Moreover, a significant difference is assuredly provided between the sensitivities of the first, second, . . . , and n-th surfaces, and quantitativeness in the dynamic range is assuredly maintained.

More specifically, if the value represented by cos θ(k−1)/cos θk is 20 at the maximum, quantitativeness is maintained more assuredly.

More specifically, if the ratio of the cosine for the largest angle to the cosine for the smallest angle, i.e., the value represented by cos θ1/cos θn is 50 at the minimum, a significant difference is more assuredly provided between the sensitivities of the respective surfaces.

The value represented by cos θ(k−1)/cos θk is preferably substantially uniform for all pairs of angles θ1, θ2, . . . , and θn.

If the value represented by cos θ(k−1)/cos θk is substantially uniform for all pairs of the angles θ1, θ2, . . . , and θn, a uniformly quantitative dynamic range is realized.

It is sufficient that there are provided the first, second, . . . , and n-th surfaces forming the respective angles θ1, θ2, . . . , and θn and having the above-described specific relationships therebetween. That is, more surfaces forming other angles may also be included.

The present invention is also directed to a method of manufacturing a probe array.

A method of manufacturing the probe array according to the first preferred embodiment includes preparing the probe-carrying substrate and the base member, bonding the probe molecules to the probe carriers of the probe-carrying substrate, and attaching the probe-carrying substrate onto the seating surface of the base member, with the second principal surface of the probe-carrying substrate facing the seating surface.

The bonding of the probe molecules to the probe carriers may be performed before or after the attaching of the probe-carrying substrate onto the seating surface.

In the method of manufacturing the probe array according to the first preferred embodiment, in the case where the bonding of the probe molecules to the probe carriers is performed before the attaching of the probe-carrying substrate onto the seating surface, a plurality of probe-carrying substrates can be first prepared as a unit, and probe-molecule solutions can be provided on the unit of probe-carrying substrates. In this state, the relative positions between the probe-carrying substrates are strictly defined. Therefore, successive provisions of the probe-molecule solutions on the plurality of probe-carrying substrates can be performed easily.

Whereas, in the case where the bonding of the probe molecules to the probe carriers is performed after the attaching of the probe-carrying substrate onto the seating surface, the bonding of the probe molecules is performed in a latter part of the entire process of manufacturing the probe array. Therefore, the probability that the probe molecules are damaged in the steps performed after the bonding of the probe molecules can be reduced.

The preparing of the base member may include providing a groove in the seating surface. The attaching of the probe-carrying substrate onto the seating surface may include attaching the probe-carrying substrate onto the seating surface with adhesive. In the attaching of the probe-carrying substrate onto the seating surface, the groove preferably receives an excessive amount of the adhesive.

With the groove provided in the seating surface so as to receive the excessive amount of adhesive, strict control of the amount of adhesive to be applied is unnecessary.

A method of manufacturing the probe array according to the second preferred embodiment includes preparing the probe-carrying substrate, and bonding the probe molecules to the probe carriers of the probe-carrying substrate. The preparing of the probe-carrying substrate includes forming the bottom surfaces and the uprising surfaces by dry etching. The dry etching is performed such that cations in plasma are incident upon the reference surface of the probe-carrying substrate in a direction other than a direction perpendicular to the reference surface.

The preparing of the probe-carrying substrate may include preparing a flat material substrate that is to form the probe-carrying substrate, preparing a supportive substrate whose top and bottom surfaces extend in directions other than directions parallel to each other, and performing the dry etching with the material substrate being placed on the supportive substrate.

In the method of manufacturing the probe array according to the second preferred embodiment in which dry etching is employed, the bottom surfaces of the probe carriers are provided at a substantially uniform distance from the light-receiving surface. Accordingly, fluorescence observation can be performed with a substantially uniform focal length for all the probe carriers, leading to an easier detection operation.

According to a third preferred embodiment of the present invention, a method of manufacturing the probe array of the second preferred embodiment includes preparing the probe-carrying substrate, and bonding the probe molecules to the probe carriers of the probe-carrying substrate. The preparing of the probe-carrying substrate includes preparing a single-crystal silicon substrate that is to form the probe-carrying substrate, and forming the bottom surfaces and the uprising surfaces by performing anisotropic wet etching using an alkaline liquid, in a state where a principal plane of the single-crystal silicon substrate deviates from a [110] crystal orientation.

By the method of manufacturing the probe array of the second preferred embodiment in which anisotropic wet etching is employed, cut-out portions each having an uprising surface along the (111) crystal plane, which is difficult to etch, with a high aspect ratio can be provided easily.

Other features, elements, characteristics and advantages of the present invention will become more apparent from the following detailed description of preferred embodiments of the present invention with reference to the attached drawings.

DESCRIPTION OF THE PREFERRED EMBODIMENTS

Figure 1:
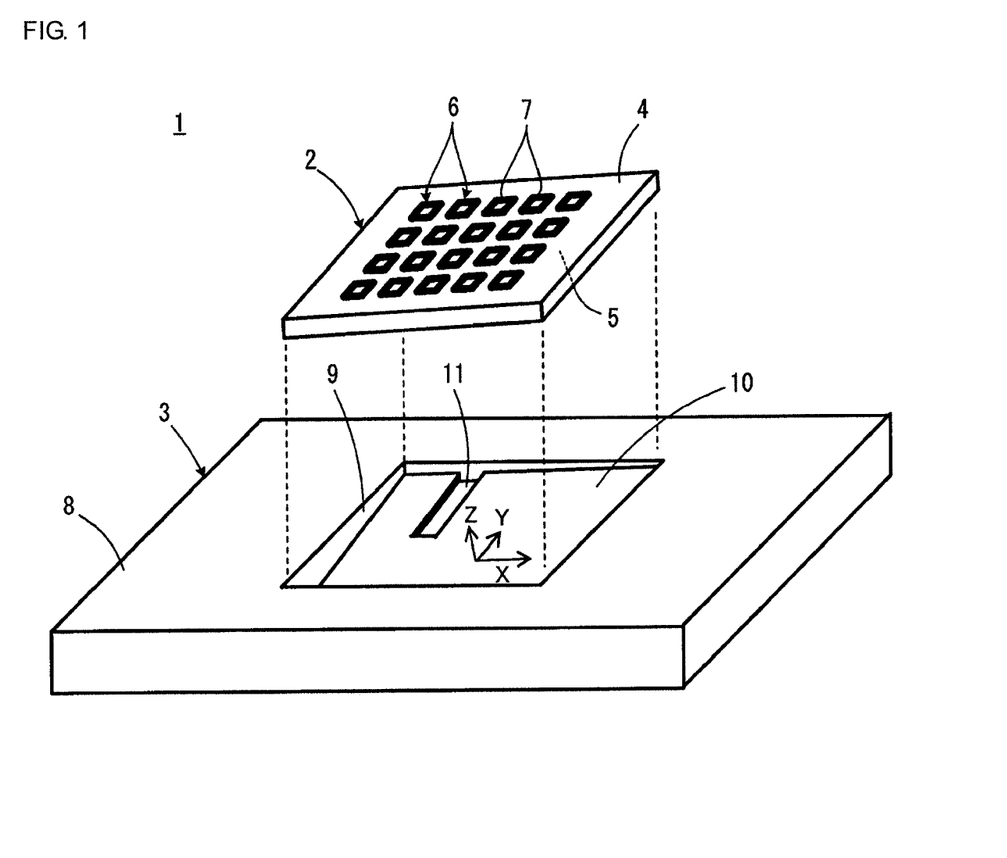
FIG. 1 is an exploded perspective view of a probe array 1 according to a first embodiment of the present invention.

FIG. 1 is an exploded perspective view of a probe array 1 according to a first embodiment of the present invention. The probe array 1 includes a probe-carrying substrate 2 and a base member 3.

The probe-carrying substrate 2 has first and second principal surfaces 4 and 5 facing and extending parallel to each other. The probe-carrying substrate 2 also has on the first principal surface 4 thereof a plurality of probe carriers 6 arranged in rows and columns. The probe carriers 6 carry probe molecules 7, as shown schematically in FIG. 1.

The base member 3 has a reference surface 8. The reference surface 8 extends parallel to a light-receiving surface (not shown) that receives, in fluorescence observation, fluorescence emitted from the probe carriers 6 of the probe array 1. The reference surface 8 has in the center thereof a recess 9. The bottom of the recess 9 forms a seating surface 10. The seating surface 10 comes into contact with the second principal surface 5 of the probe-carrying substrate 2 so as to support the probe-carrying substrate 2.

The seating surface 10 is angled with respect to the reference surface 8 so as not to be parallel thereto. When, with respect to the seating surface 10 shown in FIG. 1, the rightward direction is defined as the X axis, the backward direction is defined as the Y axis, and the upward direction perpendicular to both the X and Y axes is defined as the Z axis, the normal vector of the seating surface 10 is represented by (0,0,1). The normal vector of the reference surface 8 is angled with respect to the normal vector of the seating surface 10, and is set to be, for example, (0.019,0.105,0.994).

It may be natural to define the coordinate axes with respect to the reference surface 8. However, for simple description hereinafter, the coordinate axes are set with respect to the seating surface 10.

The probe-carrying substrate 2 is attached to the seating surface 10 with adhesive, in a state where the second principal surface 5 thereof faces the seating surface 10. In this state, the probe-carrying substrate 2 is fitted in the recess 9, thereby being positioned.

The seating surface 10 has a groove 11 that receives excessive adhesive. In the first embodiment, the groove 11 reaches an end of the seating surface 10 so that adhesive that cannot be received solely by the groove 11 can flow to the outside of the seating surface 10. With the groove 11 provided in the seating surface 10, strict control of the amount of adhesive to be applied is unnecessary.

Figure 2:
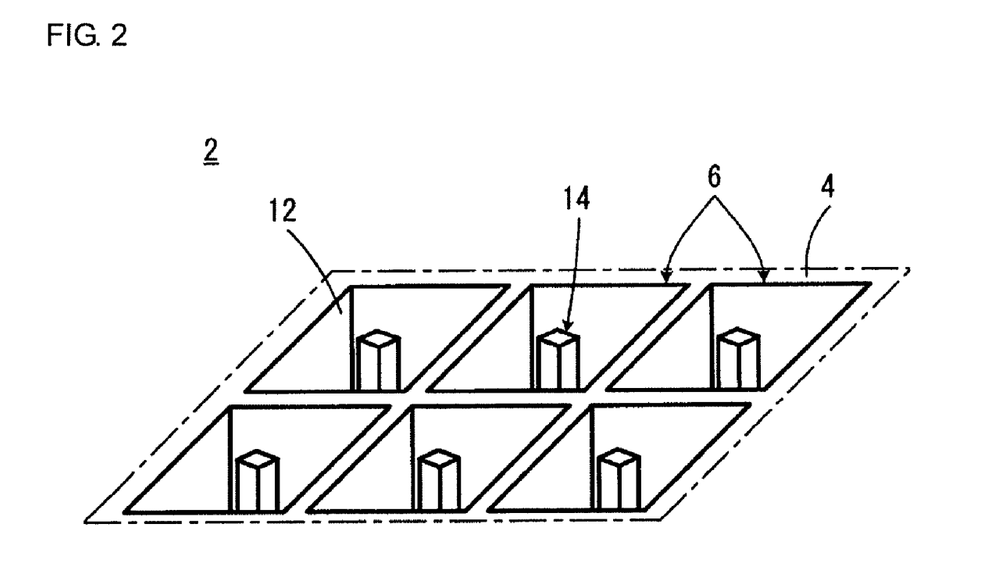
FIG. 2 is a perspective view showing a part of a probe-carrying substrate 2 included in the probe array 1 shown in FIG. 1, seen from the side of a first principal surface 4.
Figure 3:
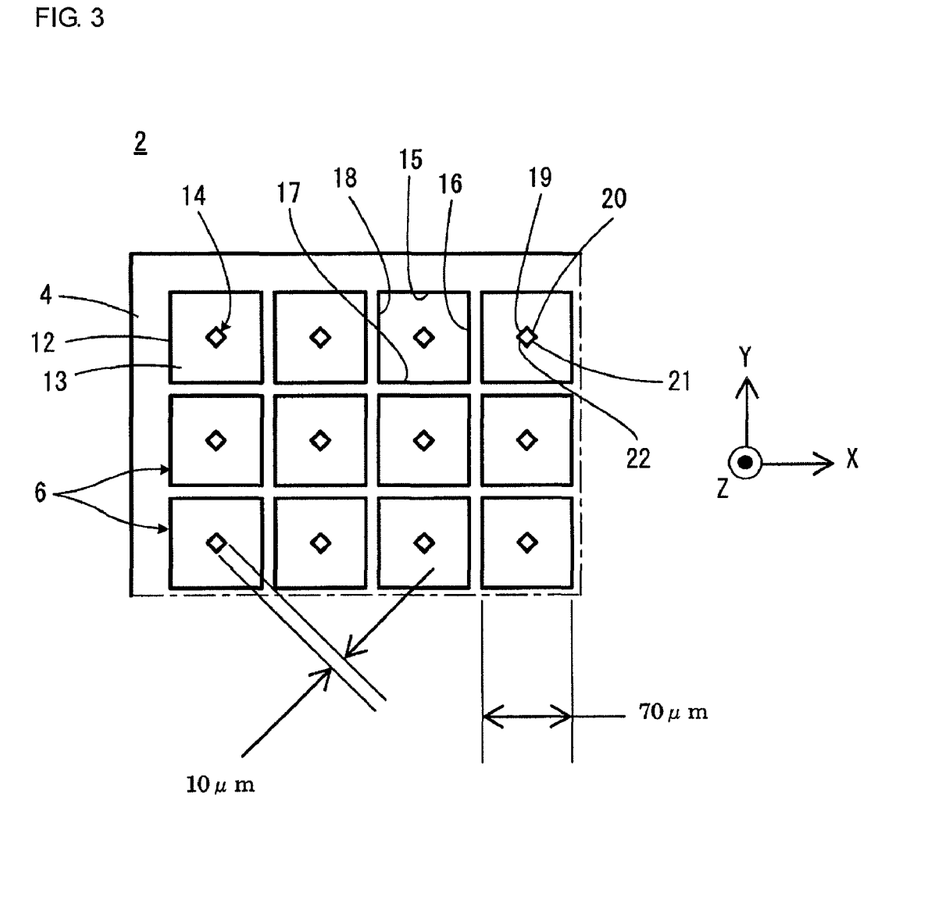
FIG. 3 is a plan view showing a part of the probe-carrying substrate 2 included in the probe array 1 shown in FIG. 1, seen from the side of a first principal surface 4.

FIGS. 2 and 3 are a perspective view and a plan view, respectively, showing a part of the probe-carrying substrate 2, seen from the side of the first principal surface 4.

As described above, the probe carriers 6 are arranged on the first principal surface 4 of the probe-carrying substrate 2. Referring to FIGS. 2 and 3, the first principal surface 4 of the probe-carrying substrate 2 is patterned with a plurality of cut-out portions 12, which are to form the probe carriers 6, each having a substantially square plan-view shape defined by four sides each having a length of, for example, about 70 μm. The cut-out portions 12 are arranged with intervals of, for example, about 10 μm therebetween. Bottom surfaces 13 of the cut-out portions 12 extend parallel to the first and second principal surfaces 4 and 5 of the probe-carrying substrate 2.

Each of the cut-out portions 12 has thereinside a projection 14 projecting from the corresponding bottom surface 13 thereof and having a substantially square cross-sectional shape defined by four sides each having a length of, for example, about 10 μm. The sides of the square defining the cut-out portion 12 and the sides of the square defining the projection 14 are not parallel to each other but are rotated with respect to each other by, for example, about 45 degrees. This gives more diverse angles to probe-molecule-carrying surfaces, which will become apparent in the description provided below.

Figure 4:
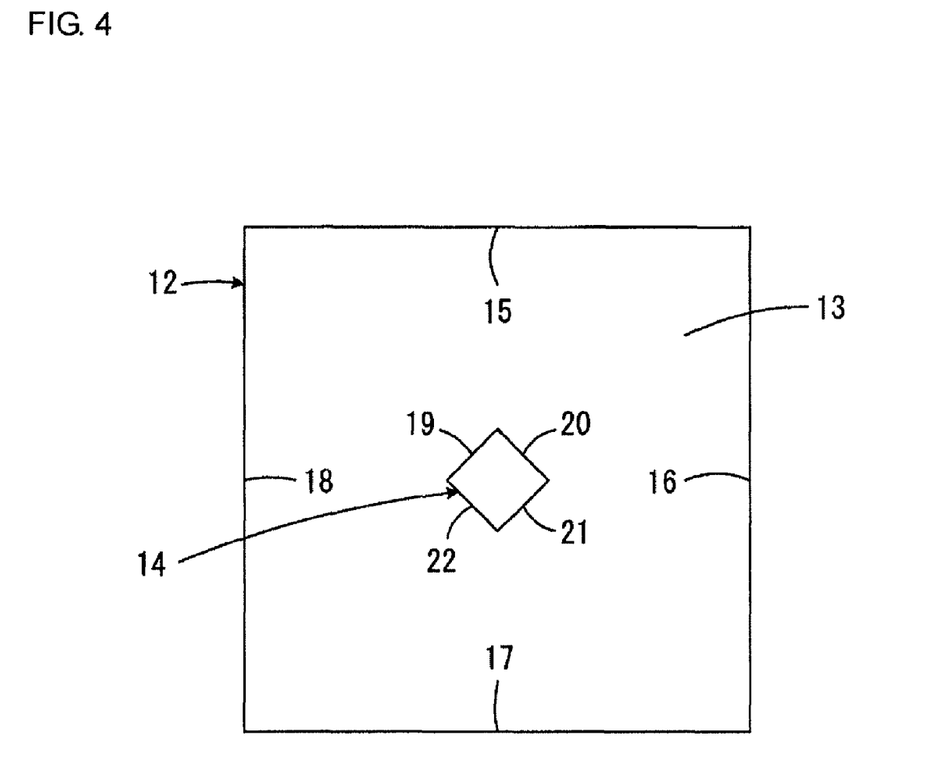
FIG. 4 is an enlarged plan view of one of cut-out portions 12 shown in FIG. 3.

FIG. 4 is an enlarged view of one of the cut-out portions 12. The cut-out portion 12 has four uprising walls, i.e., inner surfaces 15 to 18, extending upward from the bottom surface 13 in, for example, a perpendicular direction. The projection 14 has four uprising walls, i.e., projection surfaces 19 to 22, extending upward from the bottom surface 13 in, for example, a perpendicular direction. The inner surfaces 15 to 18 and the projection surfaces 19 to 22 are perpendicular to the first and second principal surfaces 4 and 5 of the probe-carrying substrate 2.

Although not shown in FIGS. 2 and 3, probe molecules are carried by at least the bottom surface 13, the inner surfaces 15 to 18, and the projection surfaces 19 to 22. The probe array 1 is configured such that each of the cut-out portions 12, which are to form the probe carriers 6, carries individually different probe molecules. If the probe molecules are DNA molecules, the probe array 1 serves as a DNA chip. If the probe molecules are antigen molecules, the probe array 1 serves as an antigen chip. If the probe molecules are antibody molecules, the probe array 1 serves as an antibody chip.

A method of manufacturing the probe array 1 will now be described. Referring first to FIGS. 5A to 5D, a method of preparing the probe-carrying substrate 2 will be described.

Figure 5A:
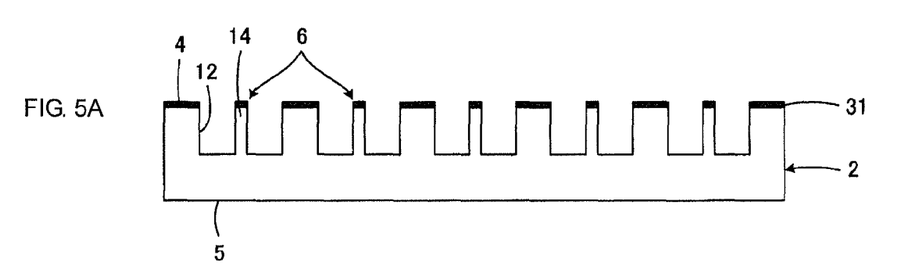
FIGS. 5A to 5D are cross-sectional views showing a process performed in preparing the probe-carrying substrate 2.

Referring to FIG. 5A, a silicon substrate as a material substrate that is to form the probe-carrying substrate 2 is prepared. The silicon substrate is photolithographically processed so as to form a resist pattern 31. Using the resist pattern 31 as a mask, the silicon substrate is etched to a depth of about 150 µm by inductive-coupling-plasma reactive-ion etching (ICP-RIE). In this manner, the cut-out portions 12 and the projections 14, i.e., the pattern of the probe-carrying substrate 2, are provided.

Figure 5B:
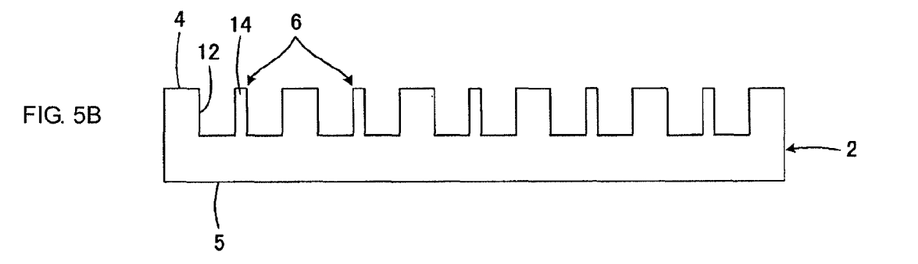

The silicon substrate patterned as the probe-carrying substrate 2 is rinsed with a mixed solution of sulfuric acid and aqueous hydrogen peroxide, whereby the resist pattern 31 is removed, as in FIG. 5B. Further, the silicon substrate, which is to form the probe-carrying substrate 2, is rinsed with a mixed solution of aqueous ammonia and aqueous hydrogen peroxide, whereby contaminations on the surface of the silicon substrate are removed, and at the same time a silicon oxide film is formed thereon. Then, the silicon substrate is then immersed in an aqueous aminosilane solution, whereby OH groups (silanol groups) at the topmost position on the surface of the silicon substrate are replaced by amino groups. Further, with a reagent containing N-(6-maleimidocaproyloxy)succinimide, the amino groups at the topmost position on the surface of the silicon substrate are replaced by maleimide groups.

Figure 5C:
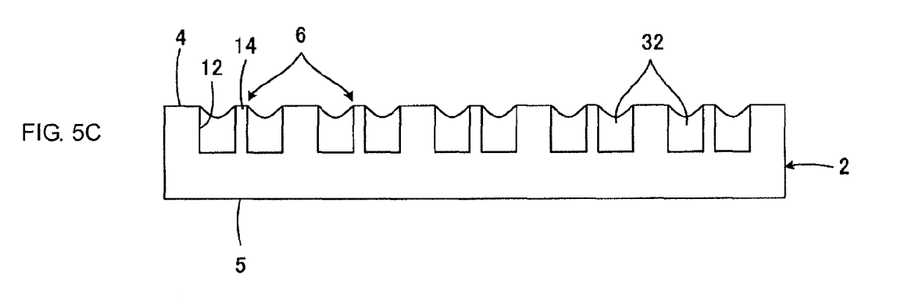

Subsequently, referring to FIG. 5C, probe-molecule solutions 32 are supplied into the cut-out portions 12, which are to form the probe carriers 6, such that probe molecules contained in the probe-molecule solutions 32 supplied to different cut-out portions 12 differ from each other. The probe-molecule solutions 32 can be supplied into the cut-out portions 12 by, for example, an ink jet method or a micropipette method, or by bringing the silicon substrate into contact with a container in which the probe-molecule solutions 32 are provided in an appropriate arrangement.

Figure 5D:
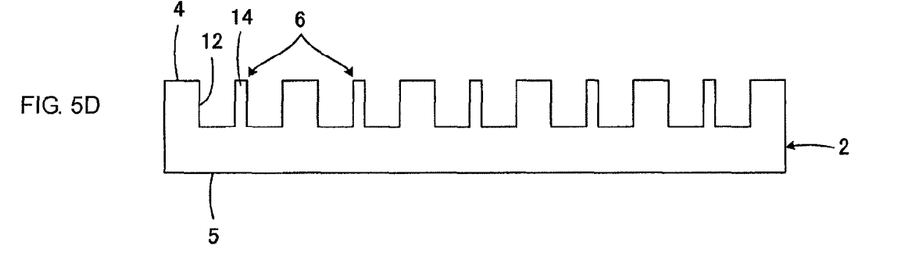

In the above step, thiol groups are introduced into the probe molecules in the probe-molecule solutions 32. When DNA molecules are used as the probe molecules, thiol groups are introduced at, for example, the 5'-ends of the DNA molecules. When polypeptide or protein molecules are used as the probe molecules, cysteine residues that have not produced disulphide bonds yet are introduced into the amino acid sequences of the molecules, for example. When the substrate is left for a certain period of time with the cut-out portions 12 thereof filled with the probe-molecule solutions 32 containing such probe molecules into which thiol groups have been introduced, the maleimide groups at the topmost position on the surface of the silicon substrate, which is to form the probe-carrying substrate 2, bond to the thiol groups of the probe molecules. As a result, the probe molecules bond to and are carried by the bottom surfaces 13, the inner surfaces 15 to 18, and the projection surfaces 19 to 22 of the cut-out portions 12, which are to form the probe carriers 6. Then, excessive liquid remaining in the cut-out portions 12 are removed. Thus, the probe-carrying substrate 2 carrying the probe molecules is completed.

Instead of utilizing the bonding between the maleimide group and the thiol group, the bonding between avidin and biotin, for example, may alternatively be utilized in bonding the probe molecules to the probe-carrying substrate 2.

The base member 3 is provided by embossing or grinding a resin substrate. After an adequate amount of adhesive is applied to the seating surface 10 of the base member 3, the probe-carrying substrate 2 prepared by the method described above is attached thereonto. Thus, the probe array 1 is completed.

In the above method, the probe molecules are first bonded to the probe-carrying substrate 2, and subsequently the probe-carrying substrate 2 is attached onto the base member 3. Alternatively, the probe-carrying substrate 2 may be first attached onto the base member 3, and subsequently the probe-molecule solutions 32 are supplied onto the probe-carrying substrate 2 so that the probe molecules are bonded to the probe-carrying substrate 2.

In a case where a plurality of probe-carrying substrates 2 are obtained by first preparing a unit of probe-carrying substrates 2 and then cutting the unit into individual pieces, it is preferable that the probe-molecule solutions 32 be provided on the unit of probe-carrying substrates 2. In such a case, the relative positions between the probe-carrying substrates 2 are strictly defined. Therefore, successive provisions of the probe-molecule solutions 32 on the plurality of probe-carrying substrates 2 can be performed easily.

In a case where the probe-carrying substrate 2 is first attached onto the base member 3 and then the probe-molecule solutions 32 are provided on the probe-carrying substrate 2, the bonding of the probe molecules is performed in a latter part of the entire process of manufacturing the probe array 1. Therefore, the probability that the probe molecules are damaged in the steps performed after the bonding of the probe molecules can be reduced.

The probe carriers 6 of the probe array 1 each have a plurality of surfaces carrying the probe molecules. The plurality of surfaces, i.e., the bottom surface 13, the inner surfaces 15 to 18, and the projection surfaces 19 to 22, are not parallel to but form individually different angles with respect to the principal surface of the probe array 1, i.e., the reference surface 8 of the base member 3.

Referring to FIG. 3, the rightward direction in the first principal surface 4 of the probe-carrying substrate 2 is defined as the X axis, the upward direction in the first principal surface 4 is defined as the Y axis, and the frontward direction perpendicular to both the X and Y axes is defined as the Z axis. In the probe array 1, the seating surface 10 of the base member 3 and the first principal surface 4 of the probe-carrying substrate 2 are parallel to each other. Accordingly, the X, Y and Z axes defined in FIG. 3 exactly coincide with the X, Y and Z axes defined with respect to the seating surface 10 in FIG. 1.

In this coordinate system, the normal vectors of the inner surfaces 17 and 18 are represented by (0,1,0) and (1,0,0), respectively, the normal vectors of the projection surfaces 19 and 20 are represented by (−1/√2,1/√2,0) and (1/√2,1/√2,0), respectively, and the normal vector of the bottom surface 13 is represented by (0,0,1).

The bottom surface 13, the inner surfaces 17 and 18, and the projection surfaces 19 and 20 are particularly mentioned here among all the surfaces 13 and 15 to 22 of the probe carrier 6 because when the aforementioned surfaces 13, 17, 18, 19, and 20 are oriented so as to face the light-receiving surface, the other surfaces 15, 16, 21, and 22 are oriented so as to face away and be hidden from the light-receiving surface.

The cosine for an angle formed between the bottom surface 13 and the principal surface of the base member 3, i.e., the reference surface 8 of the probe array 1, will now be calculated. The cosine can be calculated by dividing the inner product of the normal vector (0.019,0.105,0.994) of the reference surface 8 that is set as described above and the normal vector (0,0,1) of the bottom surface 13 by the product of the magnitude of the normal vector (0.019,0.105,0.994) of the reference surface 8 and the magnitude of the normal vector (0,0,1) of the bottom surface 13. The answer comes to 0.994.

The foregoing calculation also applies to the cosines for angles formed between the reference surface 8 and the inner surface 17, the inner surface 18, the projection surface 19, and the projection surface 20, respectively. The calculation results will be as follows, in descending order.

The cosine for the angle between the reference surface 8 and the bottom surface 13 is 0.994. The cosine for the angle between the reference surface 8 and the inner surface 17 is 0.105. The cosine for the angle between the reference surface 8 and the projection surface 20 is 0.0877. The cosine for the angle between the reference surface 8 and the projection surface 19 is 0.0608. The cosine for the angle between the reference surface 8 and the inner surface 18 is 0.0190.

As described above, the probe carriers 6 of the probe array 1 each have a plurality of surfaces carrying probe molecules, and these surfaces are not parallel to but form individually different angles with respect to the reference surface 8. Such probe-carrying surfaces at different angles exhibit individually different fluorescence intensities. A generalized mechanism of such a phenomenon will now be described with reference to FIG. 6.

Figure 6:
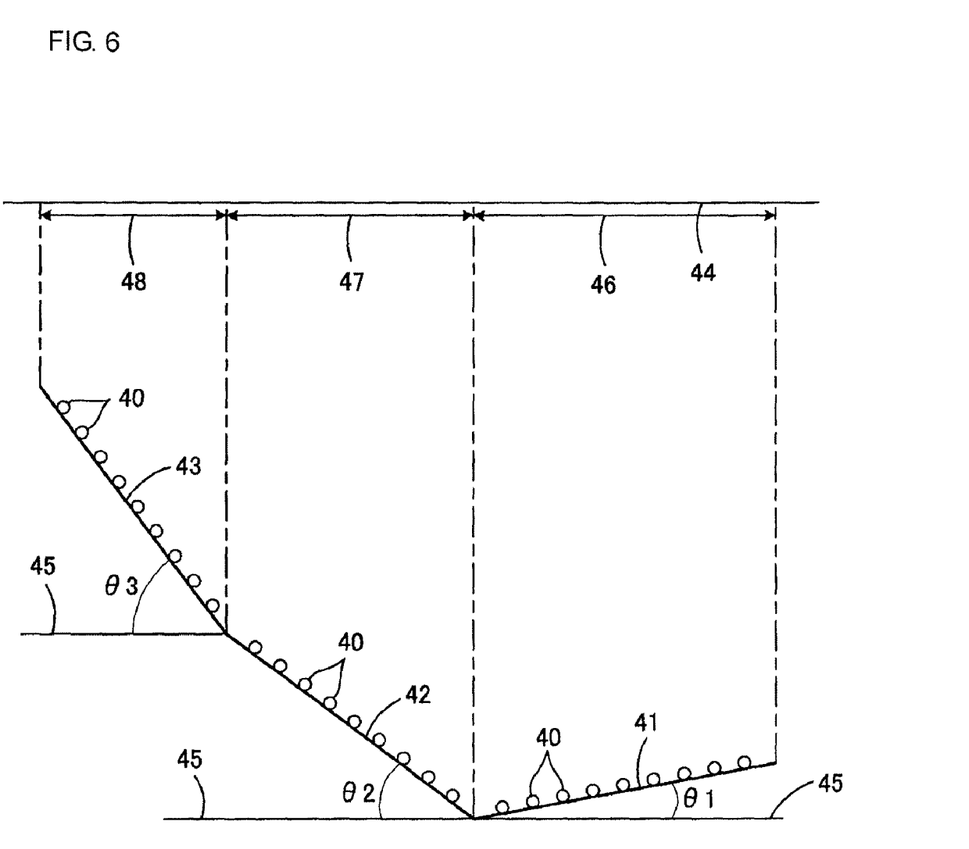
FIG. 6 is a generalized diagram showing that probe-molecule-carrying surfaces 41 to 43 forming different angles of $\theta 1$ to $\theta 3$ exhibit different fluorescence intensities.

FIG. 6 shows first to third probe-molecule-carrying surfaces 41 to 43 that carry probe molecules 40 provided with the same distribution density as each other and have the same area as each other. FIG. 6 also shows a fluorescence-receiving surface 44 positioned so as to face the first to third probe-molecule-carrying surfaces 41 to 43. With respect to a reference surface 45 extending parallel to the fluorescence-receiving surface 44, the first to third probe-molecule-carrying surfaces 41 to 43 form angles θ1, θ2, and θ3, respectively. The angles θ1 to θ3 are determined for the sides forming an angle smaller than 90 degrees, i.e., the acute-angle sides, not the obtuse-angle sides.

In a state where excitation light is applied to the first to third probe-molecule-carrying surfaces 41 to 43, fluorescently modified target molecules bonded to the probe molecules 40 are regarded as point light sources that emit fluorescence. Accordingly, the first to third probe-molecule-carrying surfaces 41 to 43 are regarded as fluorescent panels on which point light sources are arranged with given densities.

Specifically, in an observation at the fluorescence-receiving surface 44, the fluorescence emitted from the first probe-molecule-carrying surface 41 is received in an area occupied by a light-receiving section 46, the fluorescence emitted from the second probe-molecule-carrying surface 42 is received in an area occupied by a light-receiving section 47, and the fluorescence emitted from the third probe-molecule-carrying surface 43 is received in an area occupied by a light-receiving section 48.

The light-receiving section 46 has a larger area than the light-receiving section 47, and the light-receiving section 47 has a larger area than the light-receiving section 48. Accordingly, the area in which the fluorescence emitted from the second probe-molecule-carrying surface 42 is received by the light-receiving section 47 is smaller than the area in which the fluorescence emitted from the first probe-molecule-carrying surface 41 is received by the light-receiving section 46. Therefore, the fluorescence intensity per unit area is higher in the former area than in the latter area. Further, the area in which the fluorescence emitted from the third probe-molecule-carrying surface 43 is received by the light-receiving section 48 is smaller than the area in which the fluorescence emitted from the second probe-molecule-carrying surface 42 is received by the light-receiving section 47. Therefore, the fluorescence intensity per unit area is higher in the former area than in the latter area.

That is, the fluorescence intensity per unit area is inversely proportional to the light-receiving area. According to the ratio between the areas of the light-receiving sections 46 to 48, multipliers representing the relationships between the fluorescence intensities in the respective light-receiving sections 46 to 48 can be estimated. Since the multiplier for the area of the light-receiving section 47 with respect to the area of the light-receiving section 46 is (cos θ2/cos θ1), the light-receiving section 47 is estimated to exhibit a fluorescence intensity obtained by multiplying the fluorescence intensity in the light-receiving section 46 by (cos θ1/cos θ2). Likewise, since the multiplier for the area of the light-receiving section 48 with respect to the area of the light-receiving section 47 is (cos θ3/cos θ2), the light-receiving section 48 is estimated to exhibit a fluorescence intensity obtained by multiplying the fluorescence intensity in the light-receiving section 47 by (cos θ2/cos θ3).

Focusing again on the probe array 1, the bottom surface 13, the inner surfaces 17 and 18, and the projection surfaces 19 and 20 will now be described. In this case, only the fluorescence from the foregoing surfaces, among all the surfaces 13 and 15 to 22, emitted when excitation light is applied thereto reaches the light-receiving surface.

In each probe carrier 6, the angles of the bottom surface 13, the inner surface 17, the projection surface 20, the projection surface 19, and the inner surface 18 with respect to the reference surface 8 of the probe array 1 differ from each other, ascending in that order. Accordingly, the fluorescence intensities of the surfaces 13, 17, 20, 19, and 18 also differ from each other. As calculated above, the cosines for the foregoing angles with respect to the reference surface 8 are 0.994, 0.105, 0.0877, 0.0608, and 0.0190, respectively. Considering that the fluorescence intensities are proportional to the reciprocals of the cosines, the fluorescence intensities of the foregoing surfaces 13, 17, 20, 19, and 18 are represented by a ratio of 1.01:9.52:11.4:16.4:52.6.

The ratio between the fluorescence intensities can be interpreted as the ratio between their corresponding sensitivities. That is, the probe carriers 6 of the probe array 1 each have probe-molecule-carrying surfaces having different sensitivities. Thus, the probe array 1 realizes a wide dynamic range. Specifically, when the density of target molecules is low, the inner surface 18, for example, having a relatively high sensitivity provides quantitativeness. Whereas, when the density of target molecules is so high that the fluorescence intensity of the inner surface 18 having a high sensitivity become saturated, the bottom surface 13, for example, having a lower sensitivity than the inner surface 18 provides quantitativeness in terms of fluorescence emission.

Needless to say, the probe array 1 shown in the drawings is only an exemplary probe array according to the first embodiment of the present invention. When geometric design is modified, the angles of the probe-molecule-carrying surfaces of each probe carrier can be set arbitrarily. If the cut-out portions in the probe-carrying substrate are each provided in, for example, a substantially polygonal shape instead of the substantially square shape, more variations in the angles of the probe-molecule-carrying surfaces can be provided.

If the difference between the largest angle and the smallest angle of the probe-molecule-carrying surfaces with respect to the reference surface of the probe array is too small, the dynamic range cannot be made very wide. Practically, it is not advantageous unless the ratio of the cosine for the smallest angle to the cosine for the largest angle is about 5 or larger. More preferably, the foregoing ratio is about 50 or larger.

Here, the cosines for the angles formed by the probe-molecule-carrying surfaces with respect to the reference surface of the probe array are arranged in ascending order of their corresponding fluorescence intensities. A case will be considered where, for each pair of adjacent cosines, the ratio of the preceding cosine to the succeeding cosine is too large, that is, the ratio of the fluorescence intensity corresponding to the succeeding cosine to the fluorescence intensity corresponding to the preceding cosine is too large, and there is no probe-molecule-carrying surface having an intermediate fluorescence intensity between the two. In such a case, there may be an undetectable range of density of target molecules because of the following reason: While the fluorescence intensity of the probe-molecule-carrying surface having the higher fluorescence intensity is saturated, the fluorescence intensity of the probe-molecule-carrying surface having the lower fluorescence intensity is too low to be detected.

Such an undetectable range of density of target molecules may lead to a lack of quantitativeness. To exclude any undetectable range of density from the dynamic range, the following condition needs to be satisfied: For each pair of adjacent cosines that are calculated for the angles formed by the probe-molecule-carrying surfaces with respect to the reference surface of the probe array and are arranged in ascending order of their corresponding fluorescence intensities, the ratio of the preceding cosine to the succeeding cosine is always smaller than a specific value. This specific value varies depending on the device to be used in fluorescence measurement. Assuming that a typical currently commercially available fluorescence observation device is used, the specific value is, for example, about 50 or smaller, or more desirably, about 20 or smaller.

Again, the cosines for the angles formed by the probe-molecule-carrying surfaces with respect to the principal surface of the probe array are arranged in ascending order of their corresponding fluorescence intensities. For all the pairs of adjacent cosines, if the ratios of the preceding cosines to the succeeding cosines are set to be substantially the same as each other, the quantitativeness in the dynamic range can be more preferably made uniform.

Figure 7:
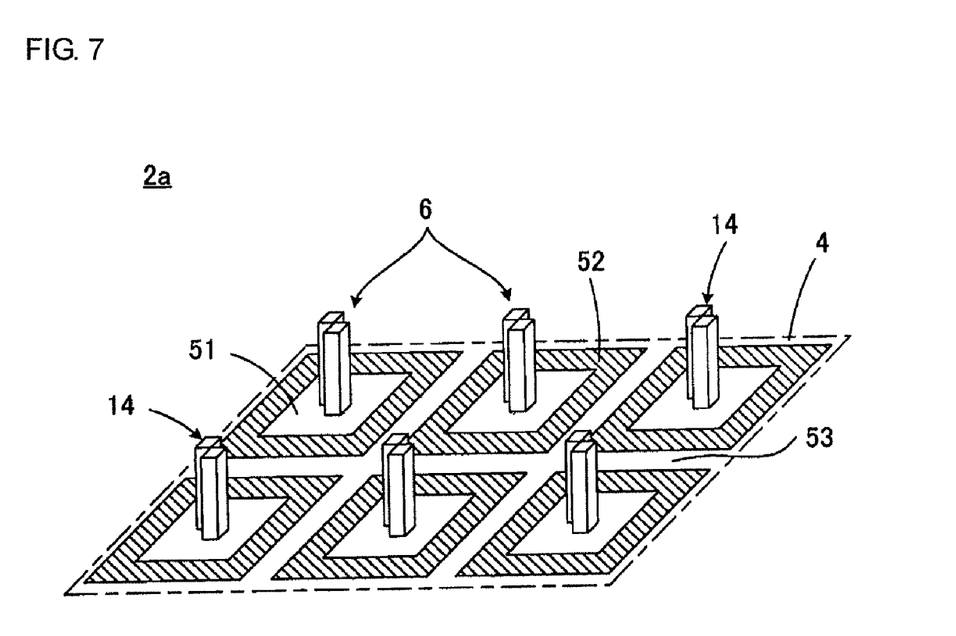
FIG. 7 is a diagram, corresponding to FIG. 2, showing a probe-carrying substrate 2a included in a probe array according to a second embodiment of the present invention.

FIG. 7, corresponding to FIG. 2, shows a probe-carrying substrate 2a included in a probe array according to a second embodiment of the present invention. In FIG. 7, elements corresponding to those in FIG. 2 are denoted by the same reference numerals as in FIG. 2, and redundant description is omitted.

A plurality of probe carriers 6 arranged on the first principal surface 4 of the probe-carrying substrate 2a do not include any cut-out portions, but each include a projection 14 having high wettability with respect to probe-molecule solutions, and a high-wettability region 51 surrounding the projection 14. The first principal surface 4 of the probe-carrying substrate 2a has a plurality of low-wettability regions 52 surrounding the respective probe carriers 6.

The first principal surface 4 of the probe-carrying substrate 2a also has checking regions 53 having high wettability with respect to probe-molecule solutions. The checking regions 53 are utilized for checking the occurrence of cross-contamination between different probe-molecule solutions provided on different probe carriers 6. The checking regions 53 are provided between adjacent probe carriers 6, thereby forming, for example, a grid pattern. The low-wettability regions 52 isolate the probe carriers 6 from the checking regions 53. After probe-molecule solutions are introduced into the probe carriers 6, the checking regions 53 provided in such a pattern are observed so as to check whether the checking regions 53 are wet, or whether there are any traces indicating that the checking regions 53 became dry after being wet. Thus, occurrence of failure due to cross-contamination between droplets of different probe-molecule solutions provided at adjacent positions can be detected with certainty.

Each of the projections 14 includes two substantially square prisms arranged diagonally such that an edge of one of the prisms is in contact with an edge of the other. The projection 14 having such a shape has eight uprising surfaces.

When the probe-carrying substrate 2a shown in FIG. 7 is compared with the probe-carrying substrate 2 shown in FIG. 2, each high-wettability region 51 corresponds to the bottom surface 13, and the eight uprising surfaces of each projection 14 correspond to the projection surfaces 19 to 22.

Figure 8:
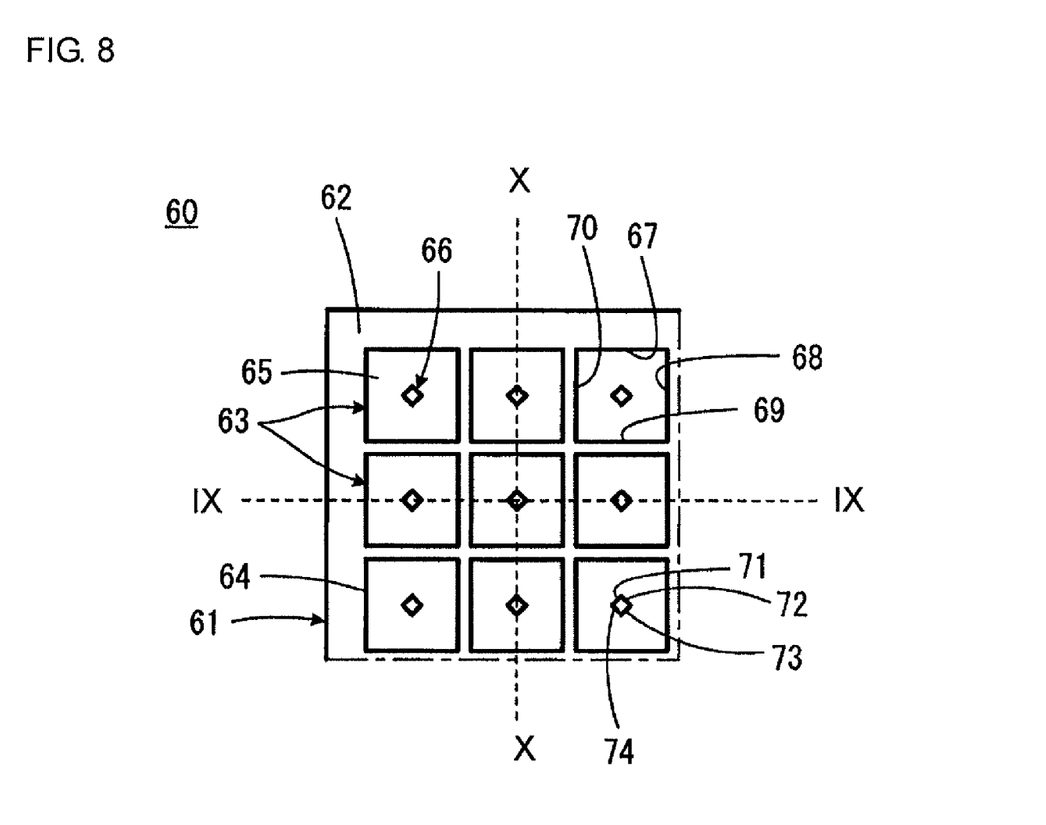
FIG. 8 is a plan view showing a part of a probe array 60 according to a third embodiment of the present invention.
Figure 9:
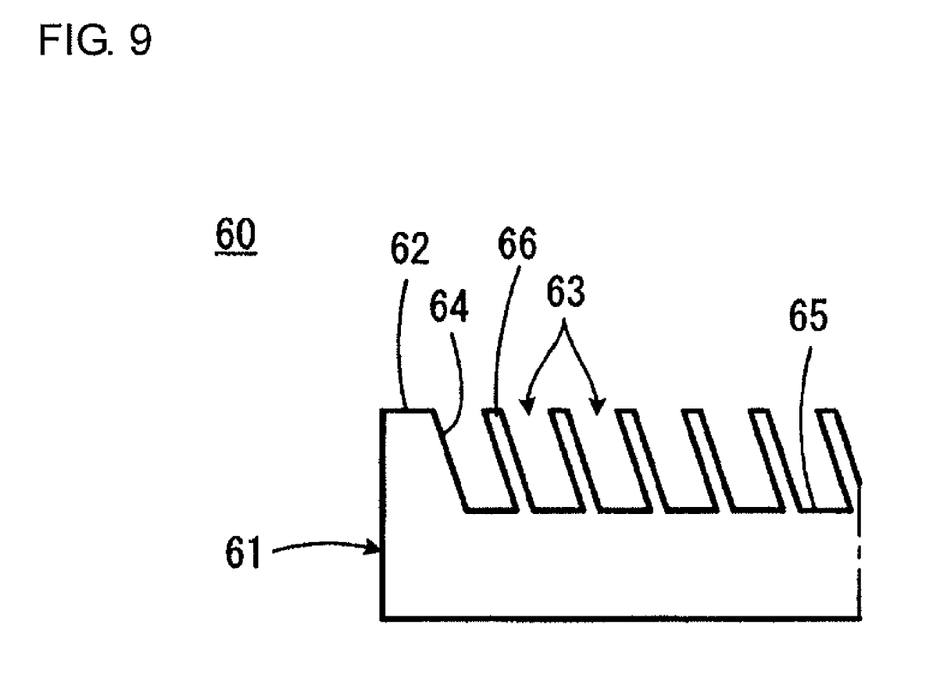
FIG. 9 is a cross-sectional view taken along the line IX-IX in FIG. 8.
Figure 10:
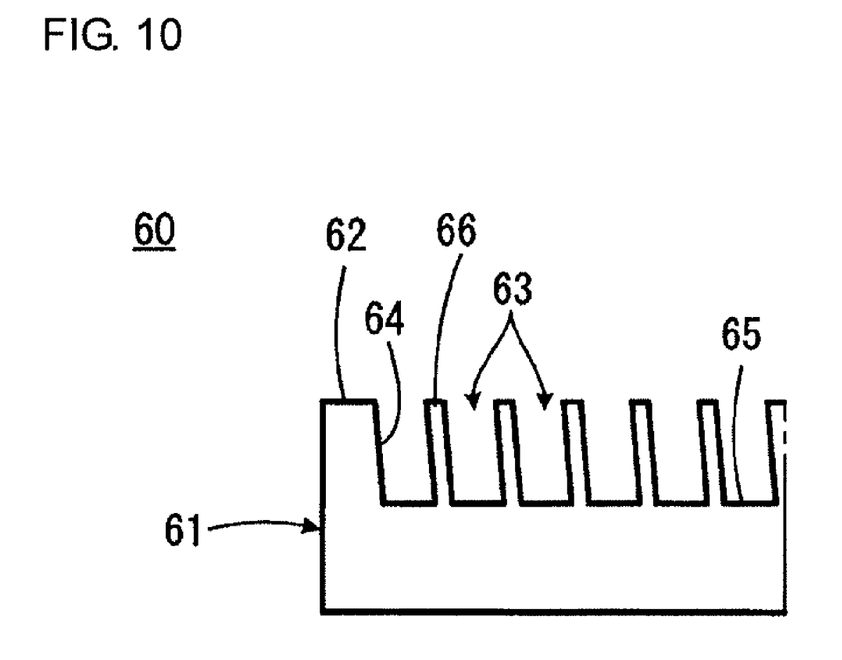
FIG. 10 is a cross-sectional view taken along the line X-X in FIG. 8.

FIG. 8 is a plan view showing a part of a probe array 60 according to a third embodiment of the present invention. FIG. 9 is a cross-sectional view taken along the line IX-IX in FIG. 8. FIG. 10 is a cross-sectional view taken along the line X-X in FIG. 8.

The probe array 60 includes a probe-carrying substrate 61. The probe-carrying substrate 61, whose principal surface serves as a reference surface 62, is provided with a plurality of probe carriers 63 arranged in rows and columns on the reference surface 62 thereof. The probe carriers 63 carry probe molecules (not shown). The reference surface 62 extends parallel to a light-receiving surface that receives, in fluorescence observation, fluorescence emitted from the probe carriers 63.

The probe carriers 63 arranged on the reference surface 62 of the probe-carrying substrate 61 are formed as a plurality of cut-out portions 64. Each of the cut-out portions 64 has a substantially square plan-view shape and includes a bottom surface 65 extending parallel to the reference surface 62 of the probe-carrying substrate 61.

The cut-out portion 64 has thereinside a projection 66 projecting from the corresponding bottom surface 65 thereof and having a substantially square cross-sectional shape. Also in the third embodiment, the sides of the square defining the cut-out portion 64 and the sides of the square defining the projection 66 are not parallel to each other but are rotated with respect to each other by, for example, about 45 degrees.

The cut-out portion 64 has four uprising surfaces, i.e., inner surfaces 67 to 70, extending from the bottom surface 65. The projection 66 has four uprising surfaces, i.e., projection surfaces 71 to 74, extending from the bottom surface 65. The inner surfaces 67 to 70 and the projection surfaces 71 to 74 extend in a direction not perpendicular to the reference surface 62 of the probe-carrying substrate 61.

Probe molecules are carried by at least the bottom surface 65, the inner surfaces 67 to 70, and the projection surfaces 71 to 74. The probe array 60 is configured such that different cut-out portions 64, which are to form the probe carriers 63, carry individually different probe molecules.

The probe array 60 having such a configuration may be used, in fluorescence observation, either by being attached onto a simple flat base member or by itself.

As described above, the probe carriers 63 of the probe array 60 each have a plurality of surfaces carrying the probe molecules. The plurality of surfaces, i.e., the bottom surface 65, the inner surfaces 67 to 70, and the projection surfaces 71 to 74, form individually different angles with respect to the reference surface 62 of the probe array 60, and therefore have individually different fluorescence intensities. Details are substantially the same as in the first embodiment and therefore will not be discussed further.

A method of preparing the probe-carrying substrate 61 included in the probe array 60 will now be described with reference to FIGS. 11A to 11D.

Figure 11A:
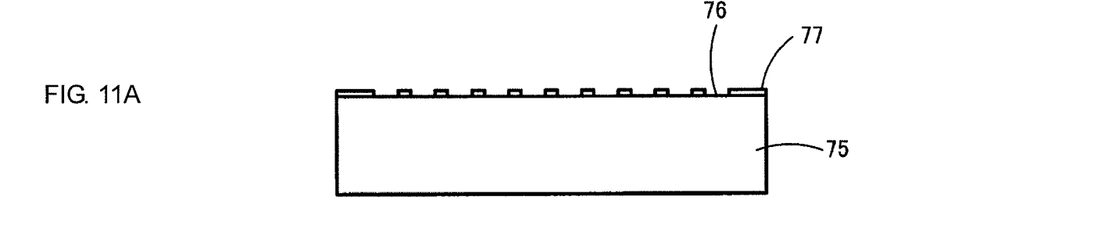
FIGS. 11A to 11D are cross-sectional views showing a process performed in preparing a probe-carrying substrate 61 included in the probe array 60 shown in FIG. 8.

Referring first to FIG. 11A, a silicon substrate 75 as a material substrate that is to form the probe-carrying substrate 61 is prepared. One principal surface 76 of the silicon substrate 75 is photolithographically processed so as to form a resist pattern 77. The principal surface 76 is to form the reference surface 62 of the probe array 60.

Figure 11B:
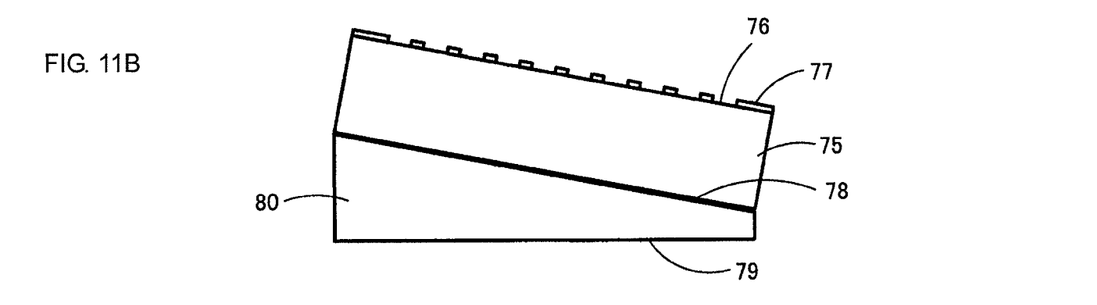

Referring now to FIG. 11B, a supportive substrate 80 is prepared. The supportive substrate 80 has a substantially wedge-like cross-sectional shape in which a top surface 78 and a bottom surface 79 thereof are not parallel to each other. The silicon substrate 75 is attached and bonded onto the supportive substrate 80.

Figure 11C:
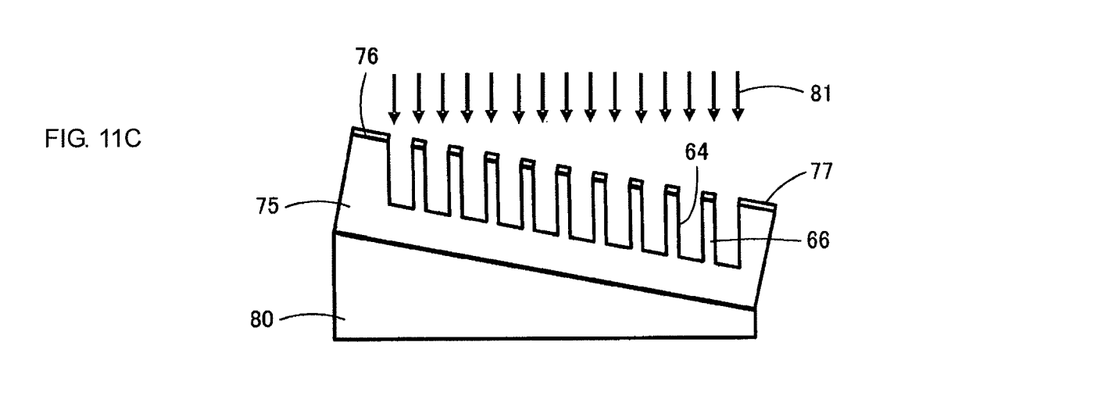

Subsequently, the silicon substrate 75 attached onto the supportive substrate 80 is placed in an ICP-RIE chamber and is etched, as shown in FIG. 11C, such that cations 81 injected during dry etching are obliquely incident upon the principal surface 76, which is to form the reference surface 62, of the silicon substrate 75. Thus, the cut-out portions 64 having walls, i.e., the inner surfaces 67 to 70 and the projection surfaces 71 to 74, extending not perpendicularly but obliquely with respect to the principal surface 76, i.e., the reference surface 62.

Figure 11D:
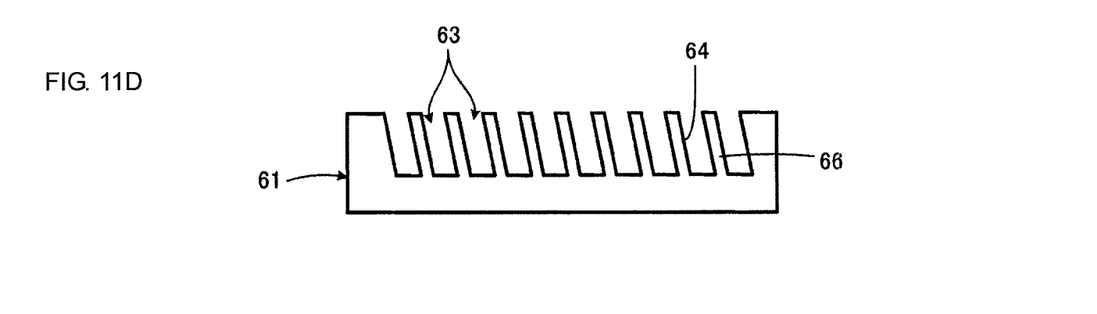

Referring now to FIG. 11D, the supportive substrate 80 is separated from the silicon substrate 75, and the resist pattern 77 is removed, whereby the probe-carrying substrate 61 is completed.

Subsequent steps including bonding of probe molecules and so forth are substantially the same as in the first embodiment and therefore will not be discussed further.

Compared with the probe array 1 of the first embodiment, the probe array 60 of the third embodiment has a disadvantage in that the manufacturing method is complicated. Instead, the probe array 60 has the following advantage. Since the bottom surfaces 65 of the cut-out portions 64 are at a substantially uniform depth with respect to the reference surface 62 of the probe array 60, the bottom surfaces 65 of all the cut-out portions 64 are positioned at a substantially uniform distance from the fluorescence-receiving surface positioned parallel to the reference surface 62 of the probe array 60. Accordingly, fluorescence observation can be performed with a substantially uniform focal length for all the probe carriers 63, leading to an easier detection operation.

In the method of manufacturing the probe array 60 according to the third embodiment, dry etching called ICP-RIE is performed in forming the cut-out portions 64 in the silicon substrate 75. The etching method is not limited to such a dry etching. Wet etching using an aqueous alkali solution, such as an aqueous potassium hydroxide solution or an aqueous tetramethylammonium hydroxide (TMAH) solution, may alternatively be employed.

If wet etching is employed, the material substrate that is to form the probe-carrying substrate 61 is preferably a single-crystal silicon substrate having a principal plane slightly deviating from the [110] crystal orientation.

If the single-crystal silicon substrate is wet-etched with an aqueous alkali solution, each cut-out portion can have an uprising surface along the (111) crystal plane, which is difficult to etch, with a high aspect ratio. By setting the single-crystal silicon substrate so as to have a principal plane in the [110] crystal orientation, two (111) crystal planes perpendicular to the principal plane are provided. By aligning sides of openings in a mask pattern, used in wet etching, along the (111) crystal planes, high-aspect-ratio cut-out portions enclosed by the (111) crystal planes can be provided.

That is, a single-crystal silicon substrate having a principal plane slightly deviating from the [110] crystal orientation is used as a material substrate that is to form the probe-carrying substrate 61, and is wet-etched with an aqueous alkali solution while a mask pattern whose openings have sides thereof aligned along the (111) crystal planes is provided on the substrate. Thus, cut-out portions having uprising surfaces extending along the (111) crystal planes not perpendicular to the principal plane can be formed.

While preferred embodiments of the invention have been described above, it is to be understood that variations and modifications will be apparent to those skilled in the art without departing from the scope and spirit of the invention. The scope of the invention, therefore, is to be determined solely by the following claims.

What is claimed is:

1. A probe array used in detecting probe molecules by fluorescence observation, the probe array comprising:
    a probe-carrying substrate having first and second principal surfaces facing and extending parallel to each other, and a plurality of probe carriers arranged on the first principal surface and carrying the probe molecules; and
    a base member having (1) a reference surface extending parallel to a light-receiving surface that receives, in the fluorescence observation, fluorescence emitted from the probe carriers, and (2) a seating surface in contact with the second principal surface of the probe-carrying substrate so as to support the probe-carrying substrate,
    wherein the probe carriers each have a bottom surface parallel to the principal surfaces, and uprising surfaces extending from the bottom surface, and
    wherein the seating surface extends in a direction other than a direction parallel to the reference surface.

2. The probe array according to claim 1,
    wherein the bottom surface and the uprising surfaces include at least a first surface forming an angle $\theta 1$ with respect to the reference surface and a second surface forming an angle $\theta 2$ with respect to the reference surface, the angle $\theta 2$ being larger than the angle $\theta 1$, the angles $\theta 1$ and $\theta 2$ being smaller than 90 degrees therebetween, and
    wherein a value represented by $\cos \theta 1 / \cos \theta 2$ is 5 at a minimum and 50 at a maximum.

3. The probe array according to claim 2, wherein the value represented by $\cos \theta 1 / \cos \theta 2$ is 5 at the minimum and 20 at the maximum.

4. The probe array according to claim 1,
    wherein the bottom surface and the uprising surfaces include at least first, second, and n-th surfaces forming respective angles $\theta 1$, $\theta 2$, and $\theta n$, with respect to the reference surface, the angles θ1, θ2, and θn being smaller than 90 degrees and being in ascending order, and wherein, when k denotes a natural number of 2 to n, a first value represented by cos θ(k−1)/cos θk for angles θ(k−1) and θk formed with respect to the reference surface by (k−1)-th and k-th surfaces is 50 at a maximum, and a second value represented by cos θ1/cos θn is 5 at a minimum.

5. The probe array according to claim 4, wherein the first value represented by cos θ(k−1)/cos θk is 20 at the maximum.

6. The probe array according to claim 4, wherein the second value represented by cos θ1/cos θn is 50 at the minimum.

7. The probe array according to claim 4, wherein the first value represented by cos θ(k−1)/cos θk is substantially uniform for all pairs of angles θ1, θ2, and θn.

8. The probe array according to claim 1, wherein the seating surface of the base member includes a groove, the groove being positioned and dimensioned to receive any excessive amount of adhesive when the probe-carrying substrate is attached onto the seating surface.

9. A method of manufacturing the probe array according to claim 1, the method comprising:
    preparing the probe-carrying substrate and the base member;
    bonding the probe molecules to the probe carriers of the probe-carrying substrate; and
    attaching the probe-carrying substrate onto the seating surface of the base member, with the second principal surface of the probe-carrying substrate facing the seating surface.

10. The method according to claim 9, wherein the bonding of the probe molecules to the probe carriers is performed before the attaching of the probe-carrying substrate onto the seating surface.

11. The method according to claim 9, wherein the bonding of the probe molecules to the probe carriers is performed after the attaching of the probe-carrying substrate onto the seating surface.

12. The method according to claim 9,
    wherein the preparing of the base member includes providing a groove in the seating surface,
    wherein the attaching of the probe-carrying substrate onto the seating surface includes attaching the probe-carrying substrate onto the seating surface with adhesive, and
    wherein, in the attaching of the probe-carrying substrate onto the seating surface, the groove receives any excessive amount of the adhesive.

13. A probe array used in detecting probe molecules by fluorescence observation, the probe array comprising:
    a probe-carrying substrate having a reference surface and a plurality of probe carriers arranged on the reference surface, the probe carriers carrying the probe molecules,
    wherein the probe-carrying substrate is disposed such that the reference surface extends parallel to a light-receiving surface that receives, in the fluorescence observation, fluorescence emitted from the probe carriers, and
    wherein the probe carriers each have a bottom surface and uprising surfaces extending from the bottom surface, the uprising surfaces extending in directions other than a direction perpendicular to the reference surface.

14. A method of manufacturing the probe array according to claim 13, the method comprising:
    preparing the probe-carrying substrate; and
    bonding the probe molecules to the probe carriers of the probe-carrying substrate,
    wherein the preparing of the probe-carrying substrate includes forming the bottom surfaces and the uprising surfaces by dry etching, and
    wherein the dry etching is performed such that cations in plasma are incident upon the reference surface of the probe-carrying substrate in a direction other than a direction perpendicular to the reference surface.

15. The method according to claim 14,
    wherein the preparing of the probe-carrying substrate includes
        preparing a flat material substrate that is to form the probe-carrying substrate;
        preparing a supportive substrate whose top and bottom surfaces extend in directions other than directions parallel to each other; and
        performing the dry etching with the material substrate being placed on the supportive substrate.

16. A method of manufacturing the probe array according to claim 13, the method comprising:
    preparing the probe-carrying substrate; and
    bonding the probe molecules to the probe carriers of the probe-carrying substrate,
    wherein the preparing of the probe-carrying substrate includes
        preparing a single-crystal silicon substrate that is to form the probe-carrying substrate; and
        forming the bottom surfaces and the uprising surfaces by performing anisotropic wet etching using an alkaline liquid, in a state where a principal plane of the single-crystal silicon substrate deviates from a [110] crystal orientation.

* * * * *